United States Patent [19]

Rosen et al.

[11] Patent Number: 5,556,377
[45] Date of Patent: Sep. 17, 1996

[54] MEDICAL PROBE APPARATUS WITH LASER AND/OR MICROWAVE MONOLITHIC INTEGRATED CIRCUIT PROBE

[75] Inventors: Arye Rosen, Cherry Hill, N.J.; Stuart D. Edwards, Los Altos, Calif.; Ronald G. Lax, Grassvalley, Calif.; Hugh R. Sharkey, Redwood City, Calif.; Ingemar H. Lundquist, Pebble Beach, Calif.

[73] Assignee: Vidamed, Inc., Menlo Park, Calif.

[21] Appl. No.: 172,448

[22] Filed: Dec. 22, 1993

Related U.S. Application Data

[63] Continuation-in-part of Ser. No. 929,638, Aug. 12, 1992, abandoned, and Ser. No. 12,370, Feb. 2, 1993, Pat. No. 5,370,675, and Ser. No. 62,364, May 13, 1993, Pat. No. 5,435,805, and Ser. No. 61,072, May 14, 1993, Pat. No. 5,385,544, and Ser. No. 61,647, May 13, 1993, Pat. No. 5,421,819.

[51] Int. Cl.$^6$ ..................................................... A61B 17/39
[52] U.S. Cl. ..................................................... 604/22
[58] Field of Search ..................... 604/53, 19–22, 604/164, 280; 601/2; 606/39, 32, 45, 47, 48; 607/96, 113, 115, 116, 138, 156, 101, 102

[56] References Cited

U.S. PATENT DOCUMENTS

| | | |
|---|---|---|
| 32,066 | 1/1886 | Leveen . |
| 1,879,249 | 9/1932 | Hansaker ............................... 604/280 |
| 1,950,788 | 3/1934 | Ewerhardt et al. . |

(List continued on next page.)

FOREIGN PATENT DOCUMENTS

| | | |
|---|---|---|
| 10858/92 | 8/1992 | Australia . |
| 0370890 | 5/1990 | European Pat. Off. . |

(List continued on next page.)

OTHER PUBLICATIONS

Application Ser. No. 07/832,115, Filed on Feb. 6, 1992.
Standard Urology Product Catalog, CIRCON ACMI: Stanford (1992).
Chang, Raymond J. et al, American Heart Journal, 125: 1276–1283 (May, 1993).

(List continued on next page.)

*Primary Examiner*—Manuel Mendez
*Attorney, Agent, or Firm*—Flehr, Hohbach, Test, Albritton & Herbert

[57] ABSTRACT

A medical probe apparatus comprising a catheter having a stylet guide housing with at least one stylet port in a side thereof and stylet guide means for directing a flexible stylet outward through at least one stylet port and through intervening tissue to targeted tissues. The stylet guide has an integrated circuit or semiconductor apparatus at the distal end thereof to generate electromagnetic radiation directly at the point of the desired target tissue. The stylet includes at least one semiconductor or integrated circuit radiation emitter adapted for electromagnetic radiation when electrically energized. An elongated electrical insulator includes proximal and distal ends adapted to be introduced into a body opening, such as the urethra. First and second elongated electrical conductors are electrically isolated by the insulator. The distal ends of the electrical conductors are connected to the semiconductor, so that electrical energy coupled to the proximal ends of the conductors energizes the semiconductor to cause radiation. In a particular embodiment of the invention, the semiconductor radiation emitter(s) is (are) a laser(s). In another embodiment, it is a microwave oscillator or integrated circuit. In yet another embodiment, two types of semiconductor radiator emitters are located distally on the catheter, and each type is connected to one of the electrical conductors. According to one aspect of the invention, a third conductor may be connected in common to both types of semiconductor radiation emitters. The stylet may include an antenna to aid in coupling radiation from a semiconductor radiation emitter to the surrounding tissue. The stylet may also include an axial aperture adapted for use with a guide filament.

24 Claims, 9 Drawing Sheets

U.S. PATENT DOCUMENTS

| | | |
|---|---|---|
| 1,968,997 | 8/1934 | Drucker . |
| 2,008,526 | 7/1935 | Wappler et al. . |
| 2,022,065 | 11/1935 | Wappler . |
| 2,047,535 | 7/1936 | Wappler . |
| 2,118,631 | 5/1938 | Wappler . |
| 2,710,000 | 6/1955 | Cromer et al. . |
| 3,230,957 | 1/1966 | Seifert . |
| 3,339,542 | 9/1967 | Howell . |
| 3,556,079 | 1/1971 | Omizo et al. ............... 128/2 |
| 3,595,239 | 7/1971 | Petersen . |
| 3,598,108 | 8/1971 | Jamshidi et al. . |
| 3,682,162 | 8/1972 | Colyer . |
| 3,828,780 | 8/1974 | Morrison, Jr. . |
| 3,835,842 | 9/1974 | Iglesias . |
| 3,840,016 | 10/1974 | Lindemann . |
| 3,850,175 | 11/1974 | Iglesias . |
| 3,858,577 | 1/1975 | Bass et al. . |
| 3,884,237 | 5/1975 | O'Malley et al. . |
| 3,924,628 | 12/1975 | Droegemueller et al. . |
| 3,939,840 | 2/1976 | Storz . |
| 3,942,530 | 3/1976 | Northeved . |
| 3,948,270 | 4/1976 | Hasson . |
| 3,991,770 | 11/1976 | Leveen . |
| 4,011,872 | 3/1977 | Komiya . |
| 4,119,102 | 10/1978 | Leveen . |
| 4,121,592 | 10/1978 | Whalley . |
| 4,136,566 | 1/1979 | Christensen . |
| 4,137,920 | 2/1979 | Bonnet . |
| 4,154,246 | 5/1979 | Leveen . |
| 4,204,549 | 5/1980 | Paglione . |
| 4,224,929 | 9/1980 | Furihata . |
| 4,228,809 | 10/1980 | Paglione ................... 128/804 |
| 4,237,898 | 12/1980 | Whalley . |
| 4,267,828 | 5/1981 | Matsuo . |
| 4,295,467 | 10/1981 | Mann et al. . |
| 4,307,720 | 12/1981 | Weber, Jr. . |
| 4,311,145 | 1/1982 | Esty et al. . |
| 4,311,154 | 1/1982 | Sterzer et al. . |
| 4,312,364 | 1/1982 | Convert et al. . |
| 4,375,220 | 3/1983 | Matvias . |
| 4,397,314 | 8/1983 | Vaguine . |
| 4,402,311 | 9/1983 | Hattori . |
| 4,405,314 | 9/1983 | Cope . |
| 4,411,266 | 10/1983 | Cosman . |
| 4,448,198 | 5/1984 | Turner . |
| 4,452,236 | 6/1984 | Utsugi . |
| 4,470,407 | 9/1984 | Hussein ........................ 606/2 |
| 4,494,539 | 1/1985 | Zenitani et al. . |
| 4,552,554 | 11/1985 | Gould et al. . |
| 4,562,838 | 1/1986 | Walker . |
| 4,565,200 | 1/1986 | Cosman . |
| 4,568,329 | 2/1986 | Mahurkar . |
| 4,580,551 | 4/1986 | Siegmund et al. . |
| 4,594,074 | 6/1986 | Anderson et al. . |
| 4,601,296 | 7/1986 | Yerushalmi . |
| 4,612,940 | 9/1986 | Kasevich et al. . |
| 4,658,836 | 4/1987 | Turner . |
| 4,660,560 | 4/1987 | Klein . |
| 4,669,475 | 6/1987 | Turner . |
| 4,672,962 | 6/1987 | Hershenson . |
| 4,676,258 | 6/1987 | Inokuchi et al. . |
| 4,681,122 | 7/1987 | Winters et al. . |
| 4,682,596 | 7/1987 | Bales et al. . |
| 4,697,595 | 10/1987 | Breyer et al. . |
| 4,700,716 | 10/1987 | Kasevich et al. . |
| 4,706,681 | 11/1987 | Breyer et al. . |
| 4,709,698 | 12/1987 | Johnston et al. . |
| 4,719,914 | 1/1988 | Johnson . |
| 4,753,223 | 6/1988 | Bremer . |
| 4,765,331 | 8/1988 | Petruzzi et al. . |
| 4,769,005 | 9/1988 | Ginsburg et al. . |
| 4,774,949 | 10/1988 | Fogarty . |
| 4,776,086 | 10/1988 | Kasevich et al. . |
| 4,781,186 | 11/1988 | Simpson et al. . |
| 4,784,638 | 11/1988 | Ghajar et al. . |
| 4,785,829 | 11/1988 | Convert et al. . |
| 4,798,215 | 1/1989 | Turner . |
| 4,800,899 | 1/1989 | Elliott . |
| 4,805,616 | 2/1989 | Pao . |
| 4,813,429 | 3/1989 | Eshel et al. . |
| 4,817,601 | 4/1989 | Roth et al. . |
| 4,818,954 | 4/1989 | Flachenecker et al. . |
| 4,822,333 | 4/1989 | Lavarenne . |
| 4,823,791 | 4/1989 | D'Amelio et al. . |
| 4,823,812 | 4/1989 | Eshel et al. . |
| 4,860,744 | 8/1989 | Johnson et al. . |
| 4,865,047 | 9/1989 | Chou et al. . |
| 4,872,458 | 10/1989 | Kanehira et al. . |
| 4,887,615 | 12/1989 | Taylor . |
| 4,893,623 | 1/1990 | Rosenbluth . |
| 4,896,671 | 1/1990 | Cunningham et al. . |
| 4,898,577 | 2/1990 | Badger . |
| 4,905,667 | 3/1990 | Foerster et al. . |
| 4,906,230 | 3/1990 | Maloney et al. . |
| 4,907,589 | 3/1990 | Cosman . |
| 4,911,148 | 3/1990 | Sosnowski et al. . |
| 4,911,173 | 3/1990 | Terwilliger . |
| 4,919,129 | 4/1990 | Weber, Jr. et al. . |
| 4,920,978 | 5/1990 | Colvin . |
| 4,932,958 | 6/1990 | Reddy et al. . |
| 4,936,281 | 6/1990 | Stasz . |
| 4,940,064 | 7/1990 | Desai . |
| 4,943,290 | 7/1990 | Rexroth ........................ 606/49 |
| 4,946,449 | 8/1990 | Davis, Jr. . |
| 4,949,706 | 8/1990 | Thon . |
| 4,950,267 | 8/1990 | Ishihara et al. . |
| 4,955,377 | 9/1990 | Lennox et al. . |
| 4,961,435 | 10/1990 | Kitagawa et al. . |
| 4,966,597 | 10/1990 | Cosman . |
| 4,967,765 | 11/1990 | Turner et al. . |
| 4,982,724 | 1/1991 | Saito et al. . |
| 4,998,932 | 3/1991 | Rosen et al. . |
| 4,998,933 | 3/1991 | Eggers et al. . |
| 5,002,558 | 3/1991 | Klein et al. . |
| 5,003,991 | 4/1991 | Takayama et al. . |
| 5,007,437 | 4/1991 | Sterzer . |
| 5,007,908 | 4/1991 | Rydell . |
| 5,010,886 | 4/1991 | Passafaro et al. . |
| 5,026,959 | 6/1991 | Ito et al. . |
| 5,029,588 | 7/1991 | Yock et al. . |
| 5,030,227 | 7/1991 | Rosenbluth et al. . |
| 5,035,695 | 7/1991 | Weber, Jr. et al. . |
| 5,035,696 | 7/1991 | Rydell . |
| 5,045,056 | 9/1991 | Behl . |
| 5,045,072 | 9/1991 | Castillo . |
| 5,055,109 | 10/1991 | Gould et al. . |
| 5,057,105 | 10/1991 | Malone et al. . |
| 5,057,106 | 10/1991 | Kasevich et al. . |
| 5,057,107 | 10/1991 | Parins . |
| 5,059,851 | 10/1991 | Corl et al. . |
| 5,060,660 | 10/1991 | Gambale et al. . |
| 5,071,418 | 12/1991 | Rosenbaum ................... 606/45 |
| 5,080,660 | 1/1992 | Buelna . |
| 5,083,565 | 1/1992 | Parins . |
| 5,084,044 | 1/1992 | Quint . |
| 5,100,423 | 3/1992 | Fearnot . |
| 5,108,415 | 4/1992 | Pinchuk et al. . |
| 5,109,859 | 5/1992 | Jenkins . |
| 5,116,615 | 5/1992 | Gokcen et al. . |
| 5,120,316 | 6/1992 | Morales et al. . |
| 5,122,137 | 6/1992 | Lennox ........................ 606/42 |
| 5,135,525 | 8/1992 | Biscoping et al. . |

| | | |
|---|---|---|
| 5,150,717 | 9/1992 | Rosen et al. . |
| 5,170,787 | 12/1992 | Lindegren . |
| 5,178,620 | 1/1993 | Eggers et al. . |
| 5,179,962 | 1/1993 | Dutcher et al. . |
| 5,190,539 | 3/1993 | Fletcher et al. . |
| 5,195,965 | 3/1993 | Shantha . |
| 5,195,968 | 3/1993 | Lundquist et al. . |
| 5,197,963 | 3/1993 | Parins .................... 606/41 |
| 5,201,732 | 4/1993 | Parins et al. . |
| 5,207,672 | 5/1993 | Roth . |
| 5,220,927 | 6/1993 | Astrahan et al. . |
| 5,222,953 | 6/1993 | Dowlatshahi . |
| 5,228,441 | 7/1993 | Lundquist . |
| 5,234,004 | 8/1993 | Hascoet et al. . |
| 5,235,964 | 8/1993 | Abenaim . |
| 5,249,585 | 10/1993 | Turner et al. .................. 607/99 |
| 5,254,088 | 10/1993 | Lundquist et al. . |
| 5,257,451 | 11/1993 | Edwards et al. . |
| 5,273,535 | 12/1993 | Edwards et al. . |
| 5,275,162 | 1/1994 | Edwards et al. . |
| 5,281,213 | 1/1994 | Milder et al. . |
| 5,281,217 | 1/1994 | Edwards et al. . |
| 5,281,218 | 1/1994 | Imran . |
| 5,287,845 | 2/1994 | Faul et al. . |
| 5,290,286 | 3/1994 | Parins . |
| 5,293,868 | 3/1994 | Nardella . |
| 5,293,869 | 3/1994 | Edwards et al. . |
| 5,299,559 | 4/1994 | Bruce et al. . |
| 5,300,068 | 4/1994 | Rosar et al. . |
| 5,300,069 | 4/1994 | Hunsberger et al. . |
| 5,300,070 | 4/1994 | Gentelia et al. . |
| 5,300,099 | 4/1994 | Rudie . |
| 5,301,687 | 4/1994 | Wong et al. . |
| 5,304,134 | 4/1994 | Kraus et al. . |
| 5,304,214 | 4/1994 | Deford . |
| 5,309,910 | 5/1994 | Edwards et al. . |
| 5,313,943 | 5/1994 | Houser et al. . |

FOREIGN PATENT DOCUMENTS

| | | |
|---|---|---|
| 0453071 | 10/1991 | European Pat. Off. . |
| 0495443 | 7/1992 | European Pat. Off. . |
| 521264A2 | 1/1993 | European Pat. Off. . |
| 2848484 | 5/1979 | Germany . |
| 3218314 | 6/1983 | Germany . |
| 3844131 | 12/1988 | Germany . |
| 3838840 | 5/1990 | Germany . |
| 2121675 | 5/1990 | Japan . |
| 9007303 | 7/1990 | WIPO . |
| WO911213 | 8/1991 | WIPO . |
| 9116859 | 11/1991 | WIPO . |
| 9207622 | 5/1992 | WIPO . |
| WO92/10142 | 6/1992 | WIPO . |
| 9221278 | 12/1992 | WIPO . |
| 9221285 | 12/1992 | WIPO . |
| 9304727 | 4/1993 | WIPO . |
| 9308755 | 5/1993 | WIPO . |
| 9308756 | 5/1993 | WIPO . |
| 9315664 | 8/1993 | WIPO . |
| 9308757 | 10/1993 | WIPO . |
| 9320767 | 10/1993 | WIPO . |
| 9320768 | 10/1993 | WIPO . |
| 9320886 | 10/1993 | WIPO . |
| 9320893 | 10/1993 | WIPO . |
| WO93/25136 | 12/1993 | WIPO . |
| 9403759 | 2/1994 | WIPO . |
| 9404222 | 3/1994 | WIPO . |
| 9405226 | 3/1994 | WIPO . |
| 9406377 | 3/1994 | WIPO . |
| 9407410 | 4/1994 | WIPO . |
| 9407411 | 4/1994 | WIPO . |
| 9407412 | 4/1994 | WIPO . |
| 9407413 | 4/1994 | WIPO . |
| 9407441 | 4/1994 | WIPO . |
| 9407446 | 4/1994 | WIPO . |
| 9407549 | 4/1994 | WIPO . |

OTHER PUBLICATIONS

Cosman, Eric R. et al, Sterostatic and Functional Neurosurgery, pp. 2490–2499 (Date Unknown).

Diasonics, Brochure DIA 2000 171 CRF May 1988.

Perinchery, Narayan, "Neoplasms of the Prostate Gland." pp. 378–409 (Date Unknown).

Urology 5th ed., Storz, Jan. 1992.

Transuretheral uwave Thermotherapy for Prostatism: Early Mayo Foundation Experience: Blute, Mayo Clinic Proceedings: vol. 67 May 92 pp. 417–421.

New Therapies for Benign Prostatic Hyperplasia, Editorial Bruskewitz, Mayo Clinic Proceedings vol. 67 May 92 pp. 493–495.

Industry Strategies, Urology: "A Multi Billion Dollar Market . . . " Stephen Scala Nov. 19, 1991 pp. 1–32.

U.I. Dept. of Health and Human Services, MMWR 41: 401–404 vol. 41, No. 23, (Jun. 12, 1992).

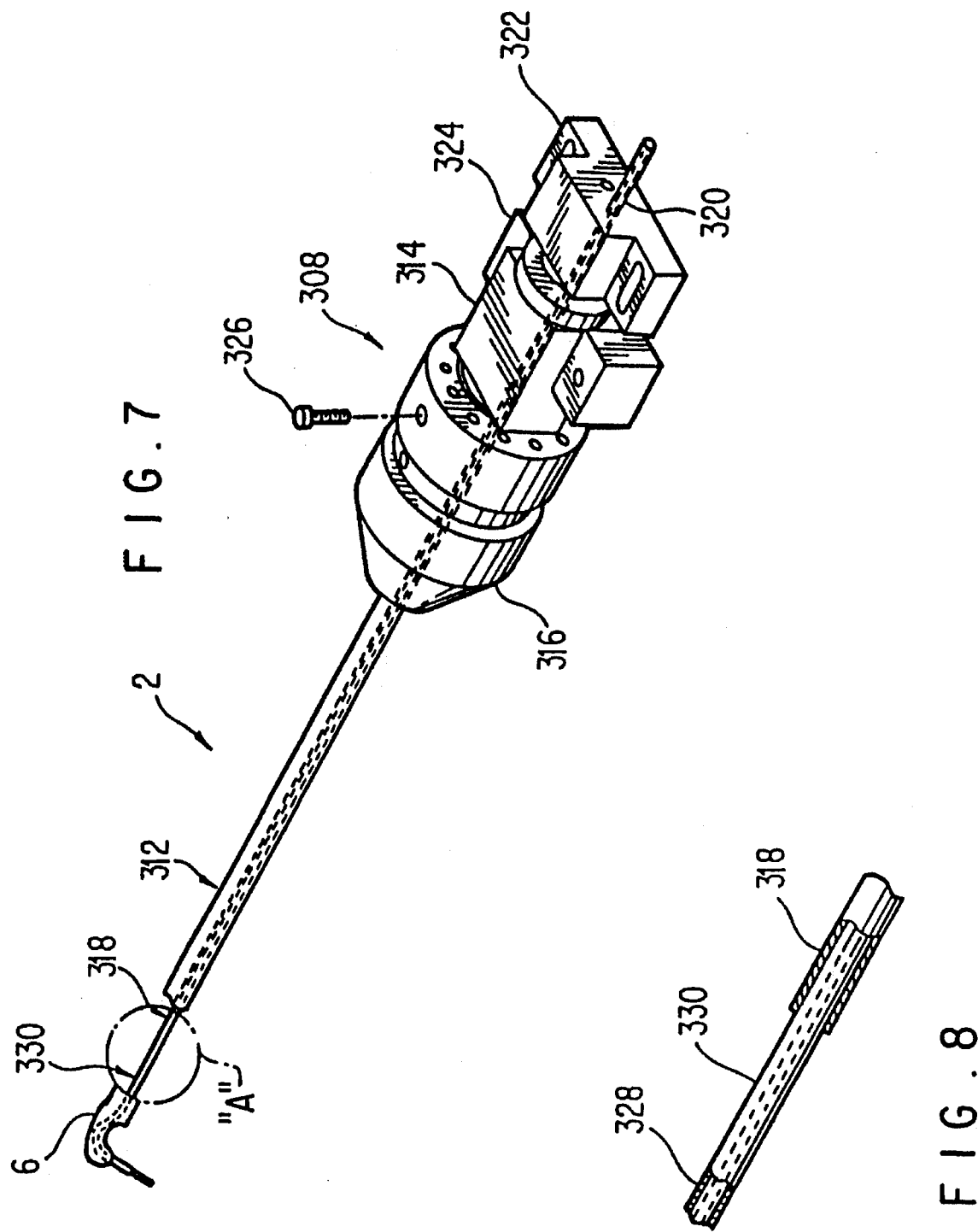

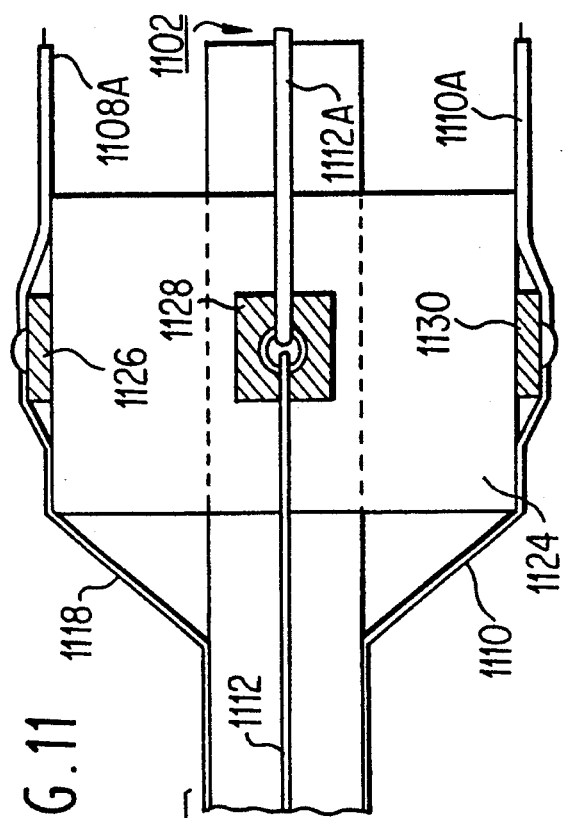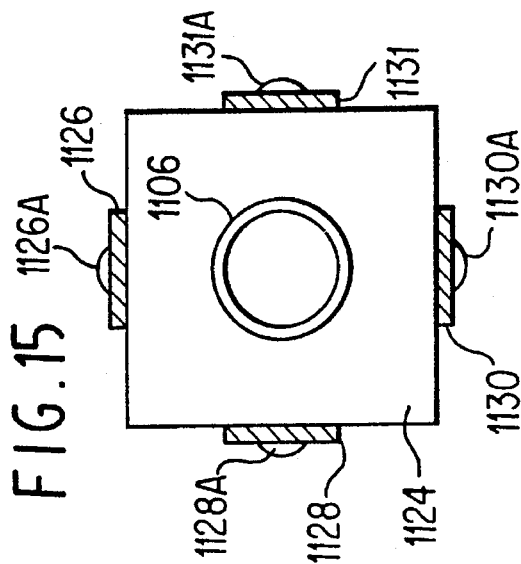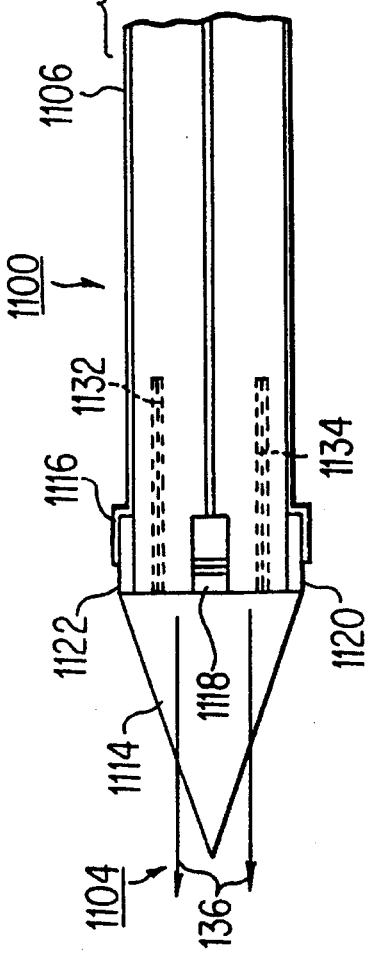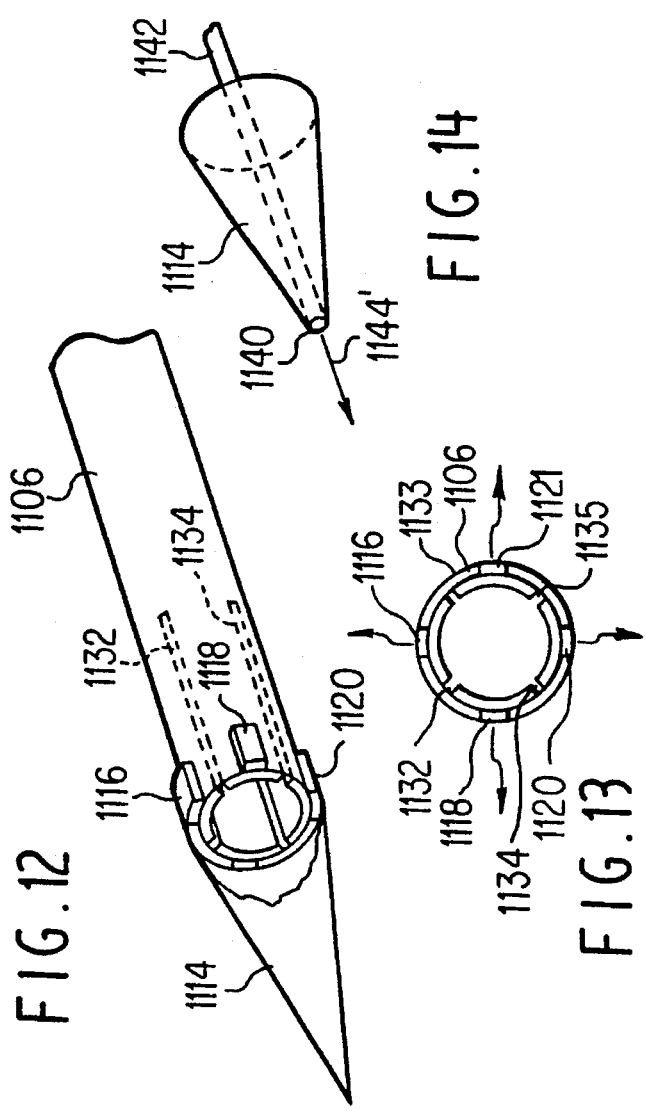

MEDICAL PROBE APPARATUS WITH LASER AND/OR MICROWAVE MONOLITHIC INTEGRATED CIRCUIT PROBE

RELATIONSHIP TO APPLICATIONS

This application is a continuation-in-part of applications Ser. No. 07/929,638 filed Aug. 12, 1992 now abandoned; Ser. No. 08/012,370 filed Feb. 2, 1993 now U.S. Pat. No. 5,370,675; Ser. No. 08/062,364 filed May 13, 1993 now U.S. Pat. No. 5,435,805; Ser. No. 08/061,072 filed May 14, 1993 now U.S. Pat. No. 5,385,544, Ser. No. 08/061,647 filed May 13, 1993 now U.S. Pat. No. 5,421,819. The entire contents of all of the above applications are incorporated herein by reference.

FIELD OF THE INVENTION

This invention is directed to unique apparatus and methods for penetrating body tissues for medical purposes such as tissue ablation and fluid substance delivery, for example. The device penetrates tissue to the precise target selected in order to deliver energy to the tissue and/or deliver substances. It limits this treatment to the precise preselected site, thereby minimizing trauma to normal surrounding tissue and achieving a greater medical benefit. This device is a catheter-like device for positioning a treatment assembly in the area or organ selected for medical treatment with one or more stylets in the catheter, mounted for extension from a stylet port in the side of the catheter through surrounding tissue to the tissue targeted for medical intervention.

In particular, this invention is directed to a medical probe device provided with a semiconductor or integrated circuit chip at the distal end thereof to generate light or microwave radiation to ablate selected tissue.

BACKGROUND OF THE INVENTION

Treatment of cellular tissues usually requires direct contact of target tissue with a medical instrument, usually by surgical procedures exposing both the target and intervening tissue to substantial trauma. Often, precise placement of a treatment probe is difficult because of the location of targeted tissues in the body or the proximity of the target tissue to easily damaged, critical body organs, nerves, or other components.

Benign prostatic hypertrophy or hyperplasia (BPH), for example, is one of the most common medical problems experienced by men over 50 years old. Urinary tract obstruction due to prostatic hyperplasia has been recognized since the earliest days of medicine. Hyperplastic enlargement of the prostate gland often leads to compression of the urethra, resulting in obstruction of the urinary tract and the subsequent development of symptoms including frequent urination, decrease in urinary flow, nocturia, pain, discomfort, and dribbling. The association of BPH with aging has been shown by the incidence of BPH in 50 percent of men over 50 years of age and increases in incidence to over 75 percent in men over 80 years of age. Symptoms of urinary obstruction occur most frequently between the ages of 65 and 70 when approximately 65 percent of men in this age group have prostatic enlargement.

Currently there is no nonsurgical method for treating BPH which has proven to be effective. In addition, the surgical procedures available are not totally satisfactory. Currently, patients suffering from the obstructive symptoms of this disease are provided with few options: continue to cope with the symptoms (i.e., conservative management), submit to drug therapy at early stages, or submit to surgical intervention. More than 430,000 patients per year in the United States undergo surgery for removal of prostatic tissue. These represent less than five percent of men exhibiting clinical significant symptoms.

Those suffering from BPH are often elderly men, many with additional health problems which increase the risk of surgical procedures. Surgical procedures for the removal of prostatic tissue are associated with a number of hazards including anesthesia related morbidity, hemorrhage, coagulopathies, pulmonary emboli and electrolyte imbalances. These procedures performed currently can also lead to cardiac complications, bladder perforation, incontinence, infection, urethral or bladder neck stricture, retention of prostatic chips, retrograde ejaculation, and infertility. Due to the extensive invasive nature of the current treatment options for obstructive uropathy, the majority of patients delay definitive treatment of their condition. This circumstance can lead to serious damage to structures secondary to the obstructive lesion in the prostate (bladder hypertrophy, hydronephrosis, dilation of the kidney pelves, chronic infection, dilation of ureters, etc.), which is not without significant consequences. Also, a significant number of patients with symptoms sufficiently severe to warrant surgical intervention are therefore poor operative risks and are poor candidates for prostatectomy. In addition, younger men suffering from BPH who do not desire to risk complications such as infertility are often forced to avoid surgical intervention. Thus the need, importance and value of improved surgical and non-surgical methods for treating BPH are unquestionable.

High-frequency currents are used in electrocautery procedures for cutting human tissue, especially when a bloodless incision is desired or when the operating site is not accessible with a normal scalpel but presents an access for a thin instrument through natural body openings such as the esophagus, intestines or urethra. Examples include the removal of prostatic adenomas, bladder tumors or intestinal polyps. In such cases, the high-frequency current is fed by a surgical probe into the tissue to be cut. The resulting dissipated heat causes boiling and vaporization of the cell fluid at this point, whereupon the cell walls rupture, and the tissue is separated.

Ablation of cellular tissues in situ has been used in the treatment of many diseases and medical conditions alone or as an adjunct to surgical removal procedures. It is often less traumatic than surgical procedures and may be the only alternative where other procedures are unsafe. Ablative treatment devices have the advantage of using an electromagnetic energy which is rapidly dissipated and reduced to a non-destructive level by conduction and convection forces of circulating fluids and other natural body processes.

Microwave, radio frequency (RF), acoustical (ultrasound) and light energy (laser) devices, and tissue destructive substances have been used to destroy malignant, benign and other types of cells and tissues from a wide variety of anatomic sites and organs. Tissues treated include isolated carcinoma masses in organs such as the prostate, and glandular and stromal nodules characteristic of benign prostate hyperplasia. These devices typically include a catheter or cannula which is used to carry a radio frequency electrode or microwave antenna through a duct to the zone of treatment and apply energy diffusely through the duct wall into the surrounding tissue in all directions. Severe trauma is often sustained by the duct wall during this cellular ablation process, and some devices combine cooling systems with microwave antennas to reduce trauma to the ductal wall. For treating the prostate with these devices, for example, heat energy is delivered through the walls of the urethra into the surrounding prostate cells in an effort to ablate the tissue causing the constriction of the urethra. Light energy, typically from a laser, is delivered to prostate tissue target sites by "burning through" the wall of the urethra. Healthy cells of the duct wall and healthy tissue between the nodules and duct wall are also indiscriminately destroyed in the process and can cause unnecessary loss of some prostate function. Furthermore, the added cooling function of some microwave devices complicates the apparatus and requires that the device be sufficiently large to accommodate this cooling system.

OBJECTS AND SUMMARY OF THE INVENTION

It is one object of this invention to provide a device for penetrating tissue, through intervening tissues to the precise target tissue selected for a medical action such as tissue ablation and optional substance delivery, limiting this activity to the precise preselected site, thereby minimizing the trauma and achieving a greater medical benefit.

It is another object of this invention to provide medical probe devices with semiconductor or integrated circuit devices directly at the distal end thereof for selective ablation applications.

It is still another object of this invention to provide medical probe devices with a semiconductor laser device capable of delivering direct laser light for selective ablation applications.

It is still another object of this invention to provide medical probe devices with an integrated circuit or semiconductor device capable of delivering direct microwave energy for selective ablation applications.

It is yet another object of this invention to provide medical probe devices with an integrated circuit or semiconductor device capable of delivering electromagnetic energy such as laser light or microwave energy for selective ablation applications.

In summary, the device of this invention is a medical probe apparatus comprising a catheter having a stylet guide housing with at least one stylet port in a side thereof and stylet guide means for directing a flexible stylet outward through at least one stylet port and through intervening tissue to targeted tissues. The stylet guide has a monolithic integrated circuit or semiconductor apparatus at the distal end thereof to generate electromagnetic radiation directly at the point of the desired tissue. The stylet includes at least one semiconductor or integrated circuit radiation emitter adapted for electromagnetic radiation when electrically energized. An elongated electrical insulator includes proximal and distal ends adapted to be introduced into a body opening, such as the urethra. First and second elongated electrical conductors are electrically isolated by the insulator. The distal ends of the electrical conductors are connected to the semiconductors, so that electrical energy coupled to the proximal ends of the conductors energizes the semiconductors to cause emitted radiation. In a particular embodiment of the invention, the semiconductor radiation emitter is a laser wherein the laser or a plurality of lasers are positioned on one electrical conductor and spaced apart from the others around the periphery of the stylet. The second conductor is attached to the top of the laser. If desired, the lasers could emit light of different frequencies. In another embodiment, the radiation emitter is a microwave oscillator or integrated circuit wherein the emitted frequency would be lower than that of the emitted laser light. In yet another embodiment, two semiconductor radiator emitters are located distally on the catheter, and each is connected to one of the electrical conductors; and, according to one aspect of the invention, a third conductor may be connected in common to both semiconductor radiation emitters. The stylet may include an antenna to aid in coupling radiation from a semiconductor radiation emitter to the surrounding tissue.

BRIEF DESCRIPTION OF THE DRAWINGS

FIG. 7 is an isometric view of the adjuster block and tension tube assembly of the RF ablation catheter shown in FIG. 6;

FIG. 8 is a detailed view "A" of the tension tube connections shown in FIG. 7;

FIG. 11 is a longitudinal cross-section of a stylet arrangement for use in a catheter according to the invention;

FIG. 12 is a perspective view of the distal region of the stylet of FIG. 11;

FIG. 13 is a cross-sectional proximal view of the distal region of the stylet of FIG. 11 taken along the lines A—A in FIG. 11;

FIG. 14 is a perspective view of the sharp tip distal end of the stylet of FIG. 11 in a different configuration;

FIG. 15 is an end view of the proximal portion of the stylet of FIG. 11;

DETAILED DESCRIPTION OF THE INVENTION

Figure 1:
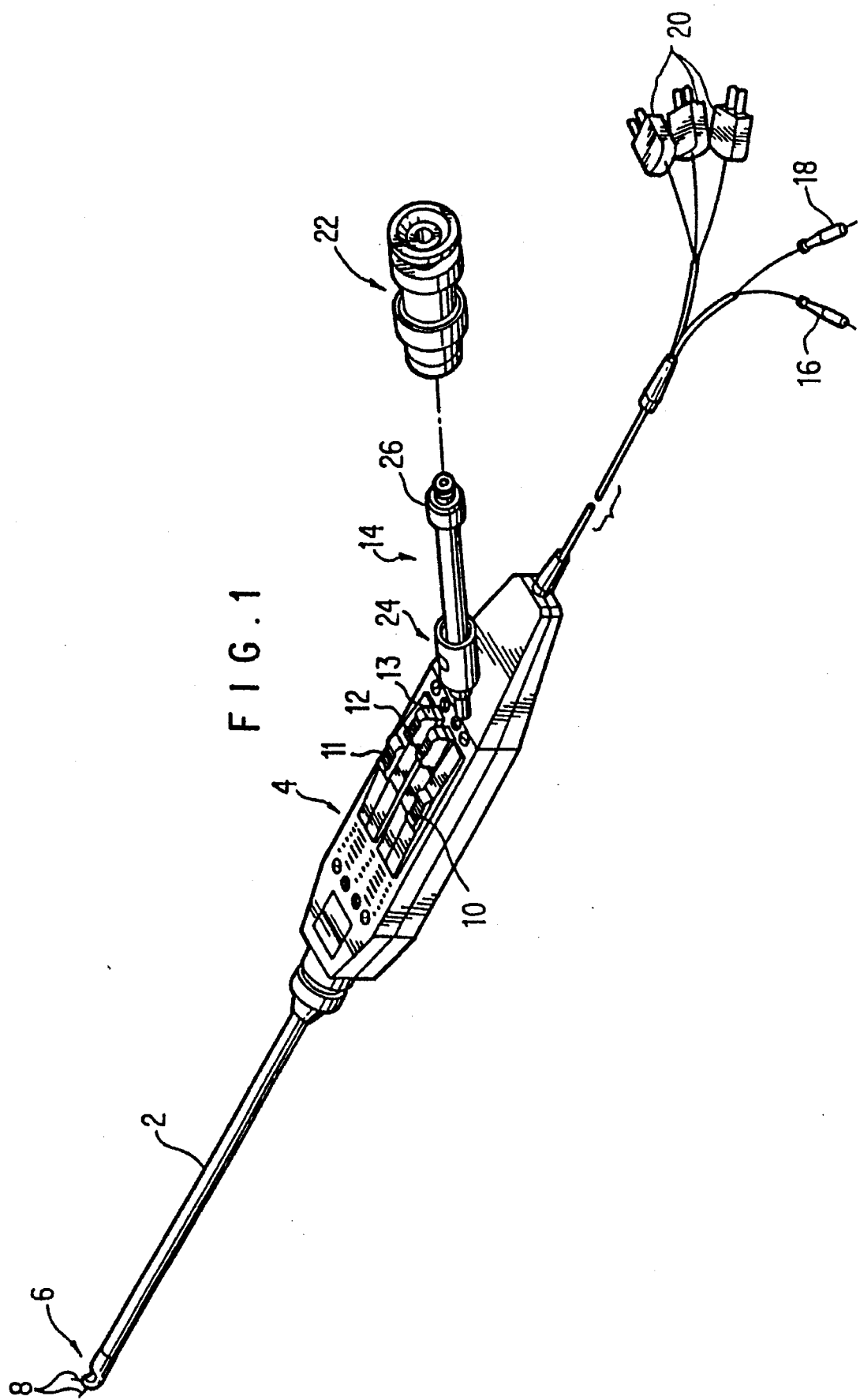
FIG. 1 is an isometric view of an RF ablation catheter embodiment with a fiber optic viewing accessory.

The device of this invention provides a precise controlled positioning of a treatment stylet in a tissue targeted for treatment, ablation, or sampling from a catheter positioned in the vicinity of targeted tissues.

The term "stylet" as used hereinafter is defined to include both solid and hollow probes which are adapted to be passed from a catheter port through normal tissue to targeted tissues. The stylet is shaped to facilitate easy passage through tissue. It can be a solid wire, thin rod, or other solid shape or it can be a thin hollow tube or other shape having a longitudinal lumen for introducing fluids to or removing materials from a site. The stylet can also be a thin hollow tube or other hollow shape, the hollow lumen thereof containing a reinforcing or functional rod or tube such as a laser fiber optic. The stylet preferably has a sharpened end to reduce resistance and trauma when it is pushed through tissue to a target site. As will be hereafter described, the stylet can also include laser light emitting, and microwave apparatus, as well.

The stylet can be designed to provide a variety of medically desired treatments of a selected tissue. As a resistance heater, radio frequency electrode, laser light emitter, or microwave antenna, it can be used to ablate or destroy targeted tissues. As a hollow tube, it can be used to deliver a treatment fluid such as a liquid to targeted tissues. The liquid can be a simple solution or a suspension of solids, for example, colloidal particles, in a liquid. Since the stylet is very thin, it can be directed from the catheter through intervening normal tissue with a minimum of trauma to the normal tissue.

The device and method of this invention provide a more precise, controlled medical treatment which is suitable for destroying cells of medically targeted tissues throughout the body, both within and external to body organs. The device and method are particularly useful for treating benign prostate hyperplasia (BPH), and the device and its use are hereinafter described with respect to BPH, for purposes of simplifying the description thereof. It will be readily apparent to a person skilled in the art that the apparatus and method can be used to destroy body tissues in any body cavities or tissue locations that are accessible by percutaneous or endoscopic catheters, and is not limited to the prostate. Application of the device and method in all of these organs and tissues are intended to be included within the scope of this invention.

BPH is a condition which arises from the benign replication and growth of cells in the prostate, forming glandular and stromal nodules which expand the prostate and constrict the opening of the prostatic urethra. Glandular nodules are primarily concentrated within the transition zone, and stromal nodules within the periurethral region. Traditional treatments of this condition have included surgical removal of the entire prostate gland, digital removal of the adenoma, as well as transurethral resection of the urethral canal and prostate to remove tissue and widen the passageway. One significant and serious complication associated with these procedures is iatrogenic sterility. More recently, laser treatment has been employed to remove tissue, limiting bleeding and loss of body fluids. Balloons have also been expanded within the urethra to enlarge its diameter, with and without heat, but have been found to have significant limitations.

Microwave therapy has been utilized with some success by positioning a microwave antenna within the prostatic urethra and generating heat in the tissue surrounding the urethra with a microwave field. Coolants are sometimes applied within the catheter shaft to reduce the temperature of the urethral wall. This necessitates complicated mechanisms to provide both cooling of the immediately adjacent tissues while generating heat in the more distant prostatic tissue. This technique is similar to microwave hyperthermia. Similarly, radio frequency tissue ablation with electrodes positioned within the urethra exposes the urethral wall to destructive temperatures. To avoid this, temperature settings required to protect the urethra must be so low that the treatment time required to produce any useful effect is unduly extended, e.g. up to three hours of energy application.

One embodiment of the device of this invention previously disclosed in a parent application uses the urethra to access the prostate and positions RF electrode stylets directly into the tissues or nodules to be destroyed. The portion of the stylet conductor extending from the urethra to targeted tissues is enclosed within a longitudinally adjustable sleeve shield which prevents exposure of the tissue adjacent to the sleeve to the RF current. The sleeve movement is also used to control the amount of energy per unit surface area which is delivered by controlling the amount of electrode exposed. Thus the ablation is confined to the tissues targeted for ablation, namely those causing the mechanical constriction. Other aspects of the invention will become apparent from the drawings and accompanying descriptions of the device and method of this invention. It will be readily apparent to a person skilled in the art that this procedure can be used in many areas of the body for percutaneous approaches and approaches through body orifices.

FIG. 1 is an isometric view of an ablation catheter embodiment of this invention with a fiber optic viewing accessory. The flexible catheter 2, attached to handle 4, has a terminal stylet guide 6 with two stylets 8. The handle has stylet sleeve tabs 10 and 11 and electrode tabs 12 and 13 as will be described in greater detail hereinafter. The handle 4 is also connected to a optical viewing assembly 14 and RF power connector 16, transponder connector 18 and thermocouple connectors 20. The portions of the catheter 2 leading from the handle 4 to the stylet guide tip 6 can optionally have a graduated stiffness. For example, the catheter can be designed to be more stiff near the handle and more flexible near the tip, or any other stiffness profiles. The catheter can be constructed of an inner slotted stainless steel tube with outer flexible sleeve such as is described in copending application Ser. No. 790,648 filed Aug. 11, 1991 (corresponding to published Australian patent application Serial No. 9210858), the entire contents of which are incorporated herein by reference. It can also be made of coiled or braided wire to which an outer sleeve is bonded.

The fiber optic viewing assembly in this embodiment includes a lens focusing assembly 22, a lens viewing assembly support connector 24 assembly attached to a male quick disconnect connector 26 by flexible tubing 28.

Figure 2:
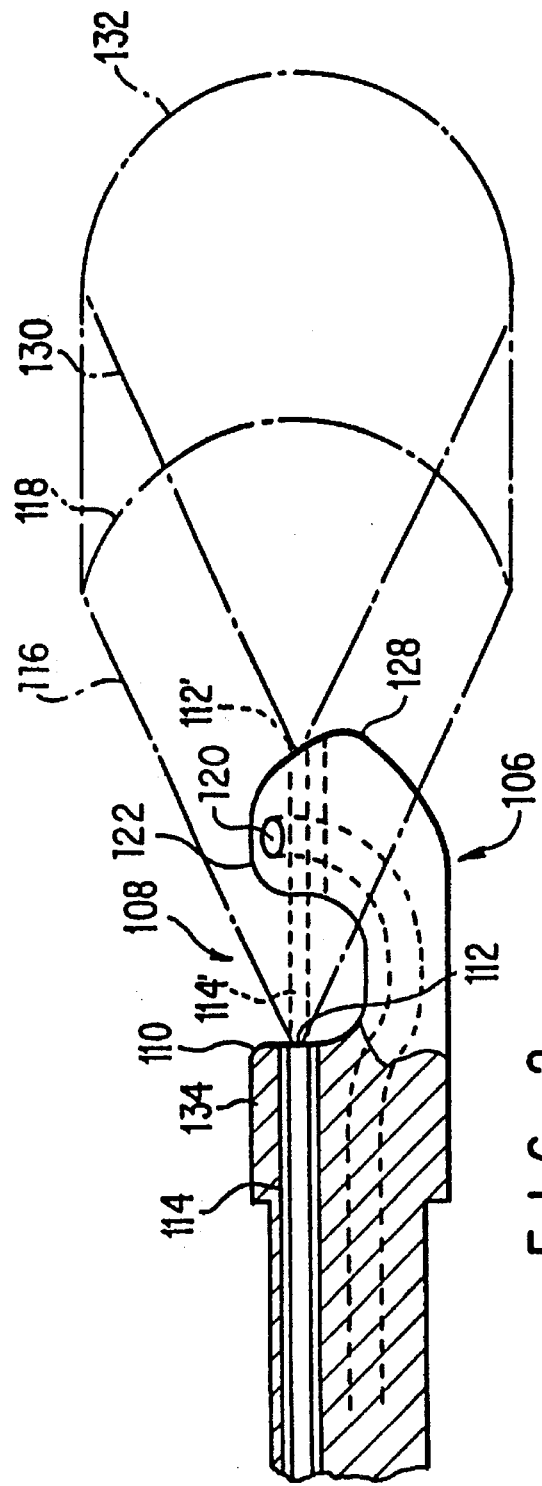
FIG. 2 is a fragmented cross-sectional view of a preferred catheter tip and stylet guide housing of this invention.

FIG. 2 is a fragmented cross-sectional view of a preferred catheter tip and stylet guide housing of this invention. The solid catheter tip 106 has a lateral depression or saddle 108 therein having a central axis approximately perpendicular to a plane through the central axis of the tip. The depression 108 has a proximal wall 110. The depression 108 can extend up to approximately half of the thickness of the housing, but at least sufficiently to unblock the viewing surface of the viewing tip 112 of the fiber optic 114. The fiber optic viewing tip 112, when positioned at the opening in wall 110, provides a field of view with lateral margins 116 and a terminal margin 118. This includes the path of stylets extended outward through ports 120.

Figure 3:
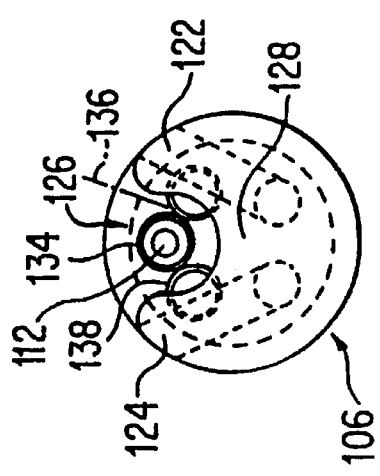
FIG. 3 is distal end view of the catheter tip and style guide housing shown in FIG. 2.

FIG. 3 a distal end view of the catheter tip and style guide housing shown in FIG. 2. The proximal end of depression 108 is split to form two projections or ears 122 and 124 which define a longitudinal or axial or longitudinal groove or saddle 126 extending from the depression 108 to the terminal tip 128 of the catheter 106. Groove 126 opens the field of view for the viewing tip 112 when in the solid line position shown in FIG. 2 and permits extension of the fiber optic and its tip through the longitudinal groove to the dotted line positions 114' and 112'. In the latter position, the field of vision has side margins 130 and a terminal margin 132. This permits the operator to examine the inner duct surfaces ahead of the catheter tip. In an alternative embodiment, the groove 126 can be replaced with a hole in the end of the tip having a size and position to permit extension of the fiber optic 114 therethrough.

The fiber optic 114 is positioned in a passageway 134 which is sufficiently larger than the fiber optic to permit flow of flushing liquid around the fiber optic to the exit in wall 110. The flushing liquid flow clears debris from the viewing tip. The inner walls of the duct (not shown) surrounding the catheter tip 106 during use confine the liquid flow, so the liquid continues to pass over the fiber optic tip even when it has been advanced to the dotted line position. Return flushing liquid lumina 136 and 138 extend through wall 110 for constant removal of contaminated flushing liquid.

Figure 4:
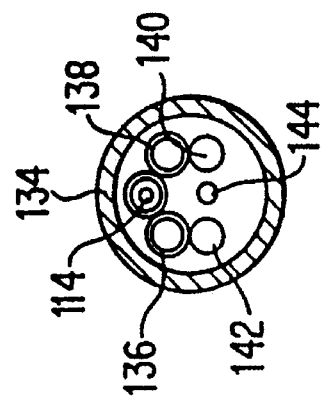
FIG. 4 is a proximal end view of the unassembled catheter tip and stylet guide housing shown in FIG. 2, showing the lumina for the components thereof.

FIG. 4 is a proximal end view of the unassembled catheter tip and stylet guide housing shown in FIG. 2, showing the lumina for the components thereof. The stylets are advanced and retracted through stylet lumina 140 and 142 to the stylet ports 120. The fiber optic is advanced and retracted through fiber optic lumen 134. The contaminated flushing fluid is removed through flushing fluid return lumina 136 and 138. Temperature sensor lumen 144 is used to house leads of a temperature sensor (not shown).

Figure 5:
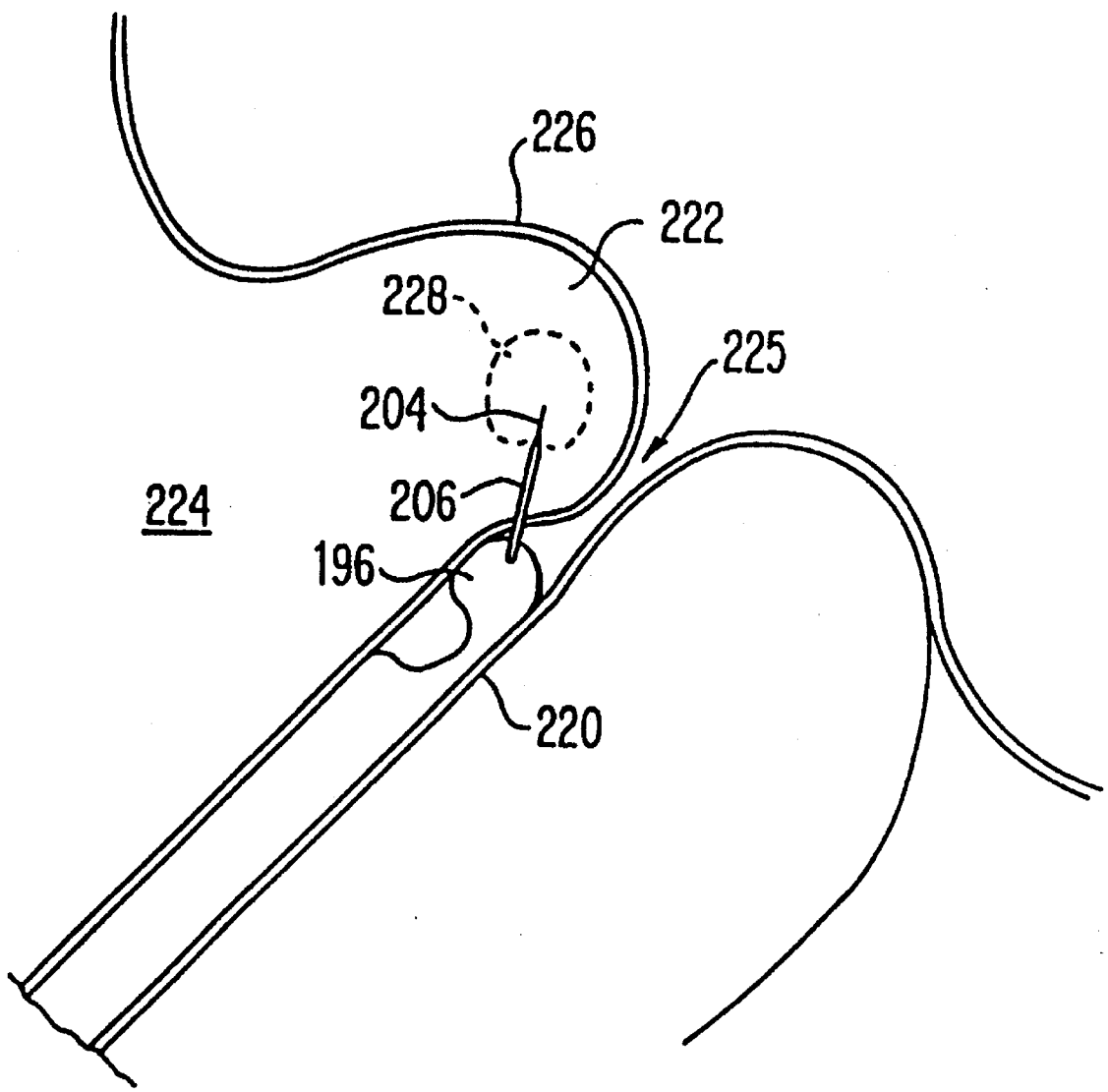
FIG. 5 is a schematic view of one manner of stylet deployment into a portion of a prostate protruding into the urinary bladder.

FIG. 5 is a schematic view of one embodiment of a single stylet of FIG. 1 or 2 shown deployed to treat a portion of a prostate protruding into the urinary bladder. The solid catheter tip 196 is positioned at the end of the urethra 220. Cell proliferation in the upper end 222 of the prostate 224 has caused it to protrude into space normally occupied by the urinary bladder, pushing a portion of the bladder wall 226 into the cavity and forming a restriction 225 beyond the end of the urethra. The stylet sleeve 206 and electrode 204 are extended at an angle of about 30° through the urethral wall into a portion of the protruded prostate, and RF current is applied to form the lesion 228. This will reduce the protruded prostate, promoting its retraction from the urethral wall and opening the restriction of the outlet end of the urethra. The catheter having a desired angle can be selected from those having predetermined angles to precisely orient the stylet and effect precise penetration of prostate tissue which extends beyond the end of the urethra, for example.

Figure 6:
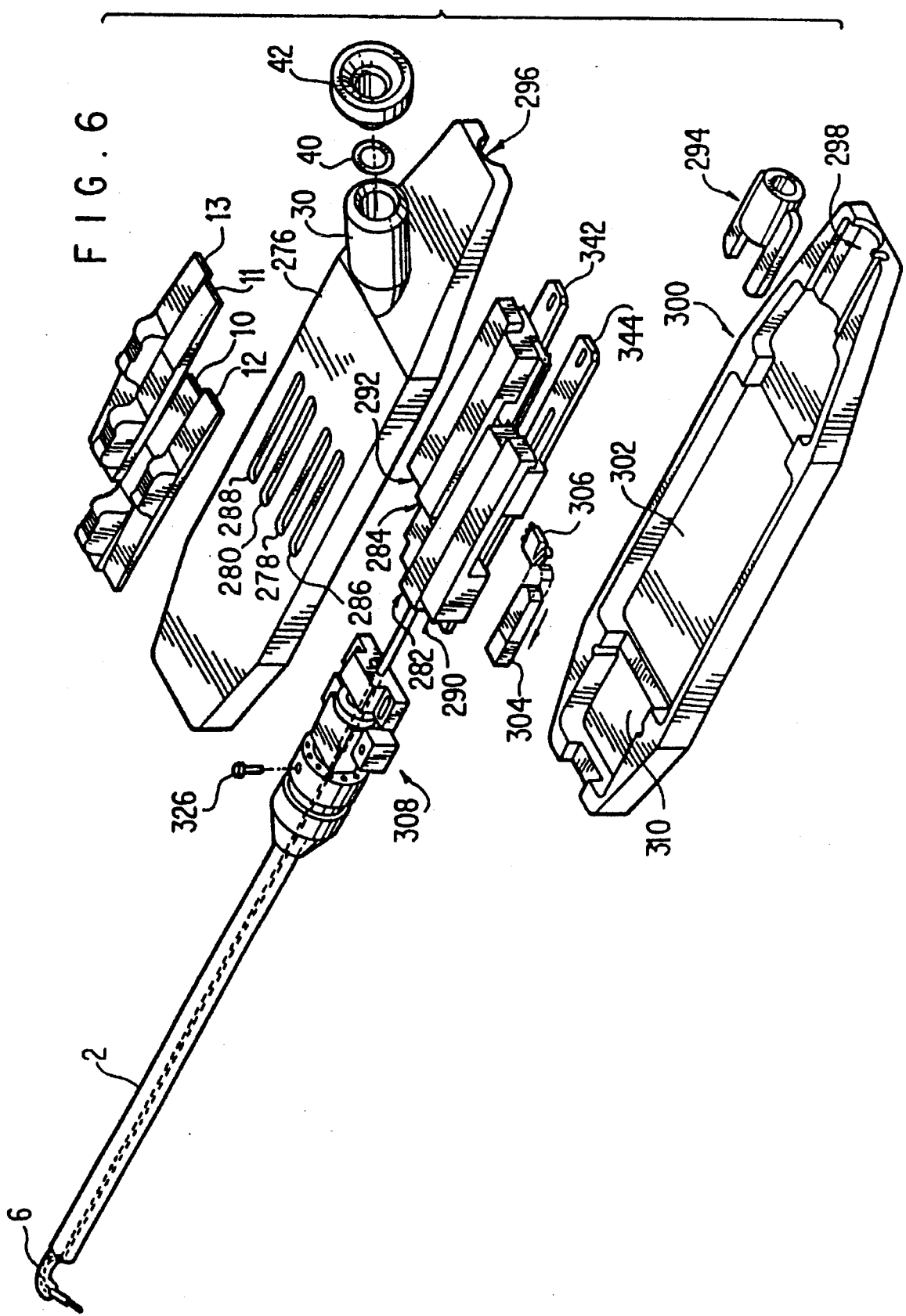
FIG. 6 is an exploded view of the RF ablation catheter shown in FIG. 1.

FIG. 6 is an exploded view of the ablation catheter assembly shown in FIG. 1. The upper handle plate 276 has two central slots 278 and 280 through which the electrode control slides 10 are attached to respective left electrode slide block 282 and right electrode slide block 284. Sleeve control slides 12 and 13 are attached through outer slots 286 and 288 to respective left sleeve slide block 290 and right sleeve slide block 292. Fiber optic receptor housing 30 is mounted on the proximal surface of the upper handle plate 276. The electrical receptor 294 is received in respective cavities 296 and 298 in the respective upper handle plate 276 and lower handle plate 300 attached thereto. The lower handle plate 300 has a central cavity 302 which accommodates the electrode and sleeve slide blocks and associated elements.

Microswitch activator blocks 304 (only left sleeve block shown) are connected to the sleeve slide blocks 290 and 292. They are positioned to actuate the microswitches 306 when the respective sleeve block (and sleeve attached thereto) have been advanced. The microswitches 306 hold the electromagnetic power circuits open until the respective sleeves are advanced to a position beyond the urethra wall and into the prostate to prevent direct exposure of the urethra to the energized electrodes. Extension of the sleeve 5 mm beyond the guide is usually sufficient to protect the urethra.

The tension-torque tube assembly 308 is mounted in the distal end of the housing in the receptor 310.

FIG. 7 is an isometric view of the adjuster block and tension tube assembly 308 of the ablation catheter shown in FIG. 6. The torque tube 312 extends from the torque coupler 314 through the twist control knob 316 to the stylet guide 6. Bending flexure of the torque tube 312 during use lengthens the path from the handle to the guide tip 6. To prevent a resulting retraction of the stylet sleeve and electrode components when the torque tube 312 is flexed, a tension tube 318 having a fixed length and diameter smaller than the inner diameter of the torque tube 312 is provided. The distal end of the tension tube 318 is securely attached to the stylet guide 6, and the proximal end 320 is secured to the adjuster block 322, for example by an adhesive. The axial or longitudinal position of the adjuster block 322 can be adjusted to insure the stylets are initially positioned just inside the outlet ports in the stylet guide 6. Torque coupler 314 is mounted on the coupler block 324. Twist control knob stop pin 326 extends into a groove (not shown) and limits rotation of the control knob 316.

FIG. 8 is a detailed view "A" of the distal end tension tube connections of the tension tube shown in FIG. 7. The tension tube 318 is securely connected to the proximal end 328 of the stylet guide 6, for example by a length of shrink tubing 330.

Figure 9:
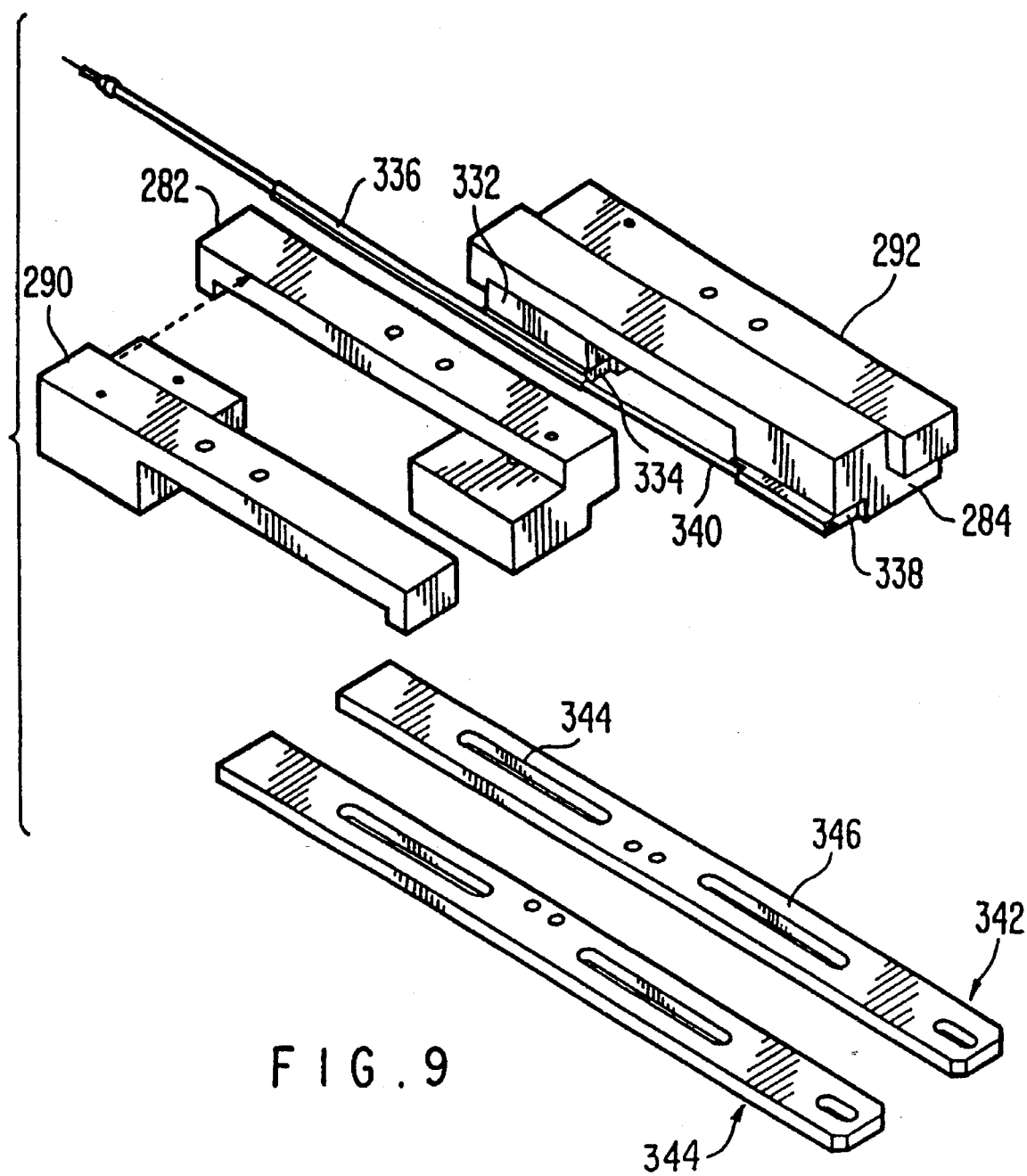
FIG. 9 is an exploded view of the sleeve and electrode slide block assembly of the embodiment shown in FIG. 6.

FIG. 9 is an exploded view of the sleeve and electrode slide block assembly of the embodiment shown in FIG. 6. The right sleeve slide block 292 has a projection 332 which extends inward under the right electrode slide block 284. Right sleeve connector 334 is mounted to the inner end of the projection 332, secured to the end of the proximal end of the sleeve 336. Right electrode connector 338 is attached to an inner surface of the electrode slide block 284 and is secured to the proximal end of electrode 340. The right sleeve and electrode slide blocks 292 and 284 are slidingly attached to the right friction adjustment rail 342 by screws (not shown) through slots 344 and 346, the screws being adjustable to provide sufficient friction between the blocks and the rail 342 to provide secure control over the stylet movement. The left sleeve slide block 290 and left electrode slide block 282 are mirror replicas of the right blocks and are similarly mounted on the left friction rail 344. The left sleeve and electrodes are not shown.

Figure 10:
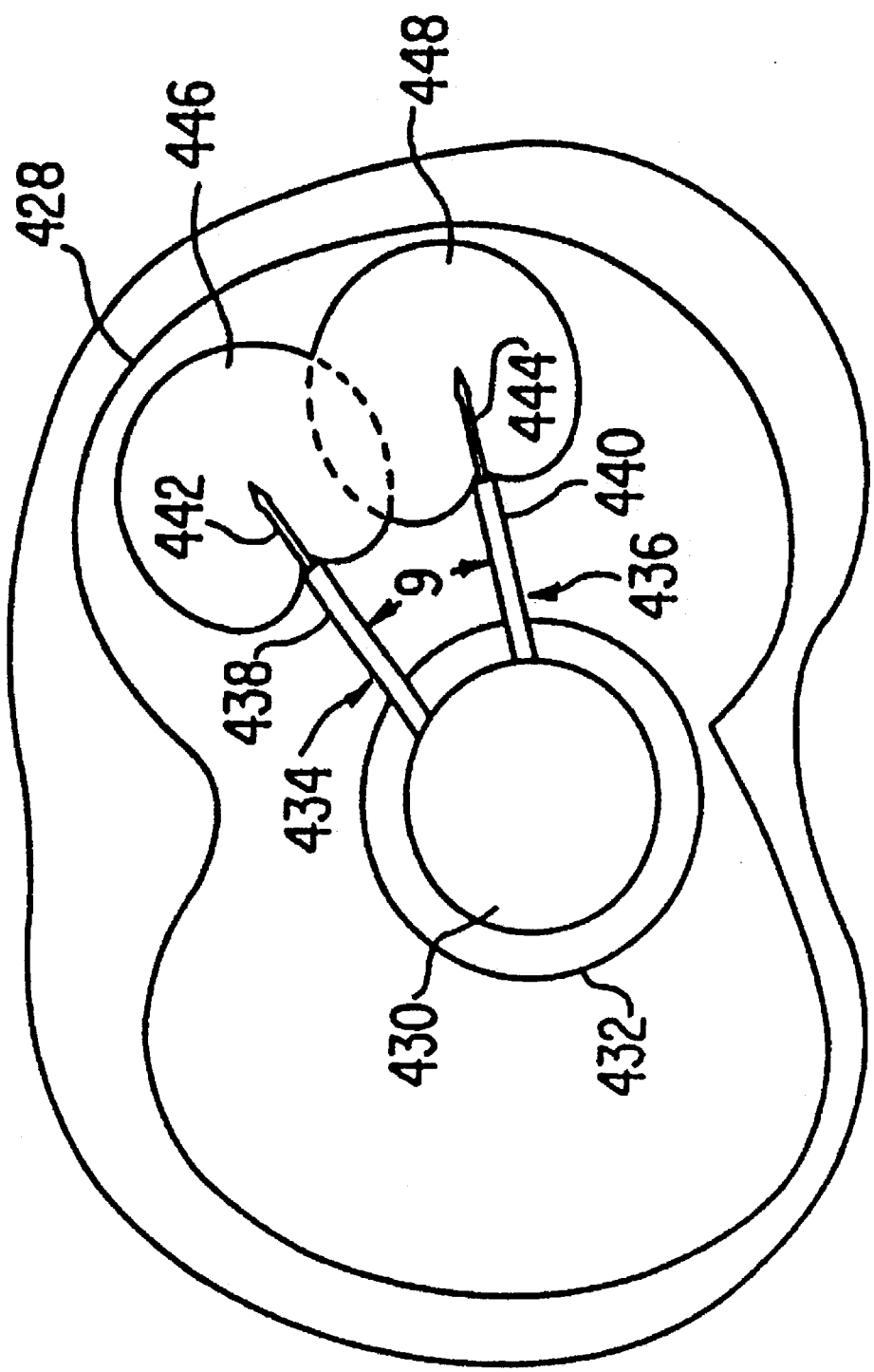
FIG. 10 is a schematic view of a deployment of two stylets in a prostate showing a stylet orientation for overlapping ablation zone method.

FIG. 10 is a schematic view of a deployment of two stylets in a prostate showing stylet orientation for overlapping ablation zone method of this invention as provided, for example, by RF current, or a microwave field. For purposes of illustration, but not by way of limitation, the prostate has been selected for this explanation, and application of this method and assembly to other areas of the body are intended to be included.

The tissues to be treated for the treatment of BPH are located in the transition zone 428 of the prostate. A catheter of this invention 430 has been inserted up the urethra 432 to a position adjacent the prostate. Two stylets 434 and 436 have been passed through the urethra wall 432 through forward movement of tabs 10 and 12 (FIG. 1) and through surrounding tissue into targeted tissues. The non-conducting sleeves 438 and 440 have been retracted by rearward movement of sleeve tabs 10 to expose a portion of the respective electrical conductors 442 and 444 at the end of each stylet. The angle between the axes of the stylets in this embodiment, "g", is less than 180°, preferably less than 110°. For most overlapping ablations, angles of 15° to 90°, and more usually from 20° to 70° are most practical. A grounding plate (not shown) is placed on the body exterior.

When electrodes 442 and 444 are supplied with RF current, the circuit from the electrodes to a grounding plate is closed. The current density flowing through the tissue passes through targeted tissues to be treated, creating lesions having the approximate cross-sectional shape of overlapping zones 446 and 448. The current density rapidly decreases as a function of distance, limiting the size of the lesions. In this manner, lesions can be caused to overlap to form a larger lesion, increasing the efficiency of the treatment. It will be readily apparent that these processes can be carried out concurrently, as described, or sequentially, and these variations are intended to be included in this invention.

The prior art has described apparatus for laser light to be generated by a laser source at the handle or at a separate instrument. The laser light would be introduced with fiber optic filaments which are then aimed or directed at the target tissue for ablation. Ablation of coronary occlusions is a well known technique for the use of laser light via optical fibers. Similarly, radio frequency or microwave sources could emanate at the operator's location with the RF or microwave energy being introduced into the conductors for generating an RF current or microwave field as the case may be. For maximum efficiency and control, however, the operative element should be closest to the site of the targeted tissue. This way, the laser light generation, radio frequency, or microwave emission can occur immediately adjacent the targeted tissue for improved tissue ablation. With the signal source immediately proximate to the desired targeted tissue, more accurate, more defined ablation can be manifested.

U.S. Pat. No. 4,998,932 to Rosen et al, issued Mar. 21, 1991, discloses a catheter with an integrated circuit located on the distal end of the catheter arrangement to provide electromagnetic radiation at a selected range of frequencies. The integrated circuit chip or chips may be a laser device or devices or include an oscillator for generating radiation frequencies in the laser light or microwave range. This patent is incorporated herein by reference in its entirety.

The present invention incorporates an integrated circuit at the distal end of a catheter of the type disclosed herein. This integrated circuit generates microwave or laser light energy depending on the type of semiconductor device it is and the energizing signals applied thereto.

FIG. 11 of the present application illustrates a stylet arrangement 1100 in accordance with the present invention. An elongated cylindrical electrically conductive tube 1106 extends from the proximal end 1102 to the distal end 1104. First, second, and third conductors 1108, 1110 and 1112, respectively, extend from a region near the proximal end 1102 to the distal end 1104. At the front or distal end 1104, the conductive tube 1106 ends with a sharp point or other sharp edge 1115. The conductive tube 1106 could be made of copper, while the sharp point or tip 1114 could be made of brass, but other conductive metals could be used as well. As seen in FIG. 11, the outer diameter of sharp tip 1114 is slightly larger than the outer diameter of the conductive tube 1106. This difference in outer diameter dimensions is to allow the mounting of the active electromagnetic devices in the shadow, i.e., immediately rearward, of the sharp tip 1114 to maintain the smooth, aerodynamic aspect of this stylet. Other structure configurations could similarly be used, such as providing the outer dimensions of the conductive tube 1106 being the same as the outer dimensions of the sharp tip 1114, with the electromagnetic devices embedded in separate cavities in the conductive tube 1106.

In FIG. 11, three laser devices 1116, 1118, 1120 are seen attached to the conductive tube 1106. In the embodiment shown in FIG. 11, four laser devices are mounted on the conductive tube 1106 at 90° intervals about the periphery of the conductive tube 1106, right behind the larger diameter face 1122 of the sharp tip 1114. The laser devices 1116, 1118, 1120 are mounted to the conductive tube 1106 by soldering them to the tube. Conductive adhesive could also be used, but for the best ohmic contact, soldering the lasers to the conductive tube 1106 is preferred. The operating conductors 1108, 1112, and 1110 are connected to lasers 1116, 1118, and 1120, respectively, by soldering the ends thereof to electrodes on the bodies of the lasers themselves. In the embodiment shown in FIG. 11, the conductors would be coated with an insulating material to electrically isolate the conductors from conductive tube 1106. Transformer windings typically use insulated wire and is known in the prior art. There is a fourth laser, not shown, which would be diametrically opposite that of laser 1118 in FIG. 11. This laser can be seen in conjunction with FIG. 13, to be described below.

Conductors 1108, 1112, and 1110 run back along the length of the conductive tube 1106 to end block 1124. End block 1124 is shown more accurately in cross-section in FIG. 15, later described. The physical shape of end block 1124 would be chosen for whatever mounting apparatus it would be used with in conjunction with the catheter shown and described above in conjunction with FIGS. 1 to 10. The conductors 1108, 1112, and 1110 would be attached to insulating pads 1126, 1128, and 1130, respectively. These pads serve as continuity pads for connecting the stylet arrangement 1100 to operating circuitry shown above in conjunction with FIGS. 1 to 10, but not shown in FIG. 11. Electrical leads 1108A, 1112A, and 1110A are seen in FIG. 11 to be attached to the insulating pads 1126, 1128, 1130 and electrically connected, by soldering, for example, to conductors 1108, 1112 and 1110, respectively. The fourth lead from the fourth laser, would be connected to the end block 1124 seen below in FIG. 15.

The conductors 1108, 1112, 1110 are seen to be on the conductor tube 1106 and could be mounted thereon by an insulating adhesive, for example. Inasmuch, however, as the stylet 1106 will be moving into and out of an insulating sleeve, see FIG. 5, for example, the wear and tear on the conductors 1108, 1112, and 1110 may be excessive if the conductors remain on the surface of conductor tube 1106. Thus, in another mode of this invention, the electrical conductors 1108, 1112, and 1110 could be embedded in grooves manufactured in the conductive tube 1106. These grooves would be in place in the conductor tube 1106 during manufacture thereof. When the conductors 1108, 1112, and 1110 are connected to lasers 1116, 1118, and 1120, the conductors could be pressed into the grooves, not shown, to run the conductors below the surface level of conductor tube 1106. Alternatively, the conductors 1108, 1112, and 1110 could be passed through holes in the conductor tube 1106 and passed through the central hollow core of the conductor tube 1106 back to the proximal end 1102 of the stylet arrangement 1100. The conductors could then be connected to insulating pads 1126, 1128, and 1130, as above, for connection to leads 1108A, 1112A, and 1110A for connection to external circuitry. Of course, the conductors could be extended out of the conductor tube 1106 all the way through the hollow core thereof.

Also seen in FIG. 11 are coolant ports 1132 and 1134. There would be two others on the conductor tube 1106, but are not visible in FIG. 11. These coolant ports could be used to provide for a coolant liquid, such as a saline solution, to be entered into the proximal end of the conductor tube 1106, and which would be emitted out of the distal end 1104 of the device 1100. The movement of the coolant liquid 1136 would provide cooling to the conductors 1108, 1112, and 1110, as well as lasers 1116, 1118, and 1120. This emitted liquid could also be used for injecting a desired medical liquid substance to the target area as desired by an operating physician.

The lasers themselves, 1116, 1118, 1120 could be state of the art solid state lasers as would be commercially available from Spectra Diode Labs., or Laser Diode, Inc. The type of laser utilized would determine the direction of laser light emitted from each laser and the wavelength of the light emitted. If for example, the lasers were Model SDL-2300 and SDL-3400 from Spectra Diode Labs., the laser could emit 1 watt of cw power at a wavelength of around 785–830 nm. FIG. 11 shows the laser light being emitted from the tops of lasers 1116 and 1120, respectively (surface emitting lasers), but if the lasers were the Model SDL-2300's, then the laser light would be emitted from the sides of the lasers, in a pin-wheel fashion. No limitation is seen or to be taken, however, from the choice of laser utilized. A typical laser, however, could be 0.5 mm long, 0.5 mm wide, and 3 to 4 mils thick, with a one watt output.

FIG. 12 is an isometric, or three dimensional, view of the stylet 1106 seen in FIG. 11. Also seen in FIG. 12 are the three lasers 1116, 1118, and 1120, together with coolant ports 1132 and 1134. There would also be one more laser directly opposite laser 1118 and two more coolant slits diametrically opposite the coolant ports 1132 and 1134 shown. Sharp tip 1114 is also depicted in FIG. 12.

FIG. 13 is a cross sectional view of the stylet 1106 looking through the proximal end thereof toward the distal end. Thus seen in FIG. 13 are lasers 1116, 1118, and 1120 seen also in FIGS. 11 and 12. Hidden laser 1121 is now seen in FIG. 13. Coolant ports 1132 and 1134 are indicated in FIG. 13 as are coolant ports 1133 and 1135 which were hidden in FIGS. 11 and 12. As set forth above, if the lasers 1116, 1118, 1120, 1121 were the surface emitting type, the laser light emitted from each would be radially out from the tops of each laser. However, if the lasers were of the edge emitting type, the laser light would be emitted from the side, tangentially to the surface of the stylet 1106, in pinwheel fashion. The laser light wavelength and power output could be from 670 nm SDL-7430-C to 3 µm and in the future up to 10 µm, depending on the type and size of semiconductor compound use solid state laser.

FIG. 14 is a perspective view of the sharp distal end of the stylet and shows an additional technique of directing coolant to the laser array or even directing medicinal fluid or other substance to a target tissue. Coolant 1144 would be directed into stylet 1106 back at the operator's location and passed inside stylet 1106 toward the distal end, through tube 1142 in sharp tip 1114 to the distal opening 1140. The coolant would be made to flow from the opening 1140 at a pressure determined at the operating physician's location. Alternatively, as set forth, the liquid could be a medical or medicinal fluid. Still another embodiment could have a semiconductor laser at the forward, or distal end of the sharp tip 1114. This would provide laser energy for ablation purposes not only in a full radial direction, but in a forward direction as well.

FIG. 15 is a rear, proximal view of the end block 1124, which would be from the right toward the left in FIG. 11. Stylet tube 1106 is viewed from its proximal end thereof. Also seen are insulating pads 1126, 1128, and 1130, as seen in FIG. 11. Insulating pad 1131 is also shown, having been hidden in previous figures. Solder points shown as small nibs 1126A, 1128A, 1130A, and 1131A allow the laser conductors 1108, 1112, and 1110, and the hidden conductor to be connected to wiring leads 1108A, 1112A, 1110A, and a fourth lead, not shown, to subsequent operating equipment to operate the lasers.

In operation, the catheter would be inserted into the patient's urethra as set forth above in conjunction with FIGS. 1 to 10. When the operating physician decides to deploy the laser stylet arrangement, the proper slide blocks are actuated to cause the insulating sleeve seen in the earlier figures to penetrate the intermediate tissue which, in this case, is the wall of the urethra. The sleeve, with its sharpened point, extends through the urethra wall into the prostate tissue. As set forth above, the sleeve can be extended partially or completely, depending on the amount of travel imparted to the sleeve block control seen in FIG. 1. When the operating physician has decided that the sleeve is in the proper position, the slide block for the stylet is then moved forward, thereby deploying the laser stylet probe 1106. If the physician desires the ablation effect of all the lasers, he or she can energize all the lasers around the periphery of the distal end 1104 of the stylet 1106. If the physician decides that not all the lasers have to be energized at one time, each laser can be configured by the operator to be fired or operated one at a time or in any order chosen, utilizing laser firing techniques well known in the art. FIG. 1 of the present application shows the leads 16 and 18 which, in conjunction with FIGS. 11 to 15, could be one or more leads to operate and monitor the operation of the lasers. After the lasers have been energized for the length of time desired by the operating physician, the stylet can be withdrawn into the sleeve arrangement, and the sleeve withdrawn from the prostate tissue into the catheter by operation of the slide blocks 10 to 13 as seen in FIG. 1. Then the entire catheter equipment can be completely withdrawn from the patient.

FIGS. 11 to 15 have been described with respect to four laser devices having been mounted on the stylet 1100. The four laser devices have been described above as exemplary only, a larger number or fewer number of lasers on the stylet 1100 being within the purview of the invention herein. For example, only two laser devices may be mounted on the stylet, or as many as eight or more lasers may be mounted on the stylet and still keep within the principles of the present invention. Lasers with different output light frequencies could be used, as well, for different heating effects. For a wider, cylindrical band of laser light, a longer laser could be used. That is, the length of the laser, as along the axis of the stylet 1106 could be increased. This feature is possible because lasers upwards of one centimeter in length have been fabricated with as many as 66 junctions, each of which are a source of laser light. If lasers 1116 et seq in FIG. 1 were increased in length from the nominal 0.5 mm to, say, 10 mm, then the band of laser light emitted would increase along the length of stylet 1106. If a more intense beam of laser light is desired, but with less of a cylindrical shape, more than one laser could be mounted at each position along the circumference of stylet 1106 at edge 1122 in FIG. 11. That is, increasing the depth of the lasers, rather than the length thereof, increases the intensity of the beam rather than the effective area of radiation.

Further, microwave semiconductor devices could be substituted for the laser devices. In Rosen U.S. Pat. No. 4,998,932, the patentee includes a microwave oscillator/oscillator amplifier with an antenna to heat up the surrounding coronary placque, while ablating the softened placque with an associated laser device on the same instrument. In the present invention, selective lasers could be replaced by microwave integrated circuit chips. This allows the operating physician to utilize the ablation benefits of both a microwave field and intense heating effect of a laser device.

Figure 16:
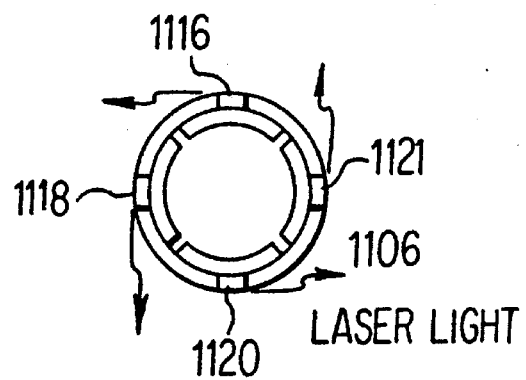
FIG. 16 is a view similar to that of FIG. 13 with the laser light emitted tangentially.

FIG. 16 shows lasers 1116, 1118, 1120 and 1121 of the edge emitting type which emits light from its side rather than the top as seen previously in conjunction with FIG. 13. The laser light arrows in FIG. 16 indicate the direction of the laser light beams in the aforementioned pin wheel fashion.

Figure 17:
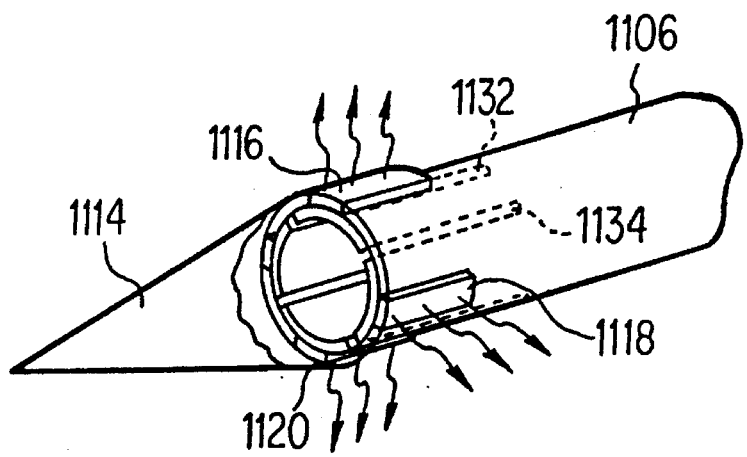
FIG. 17 is a view similar to that of FIG. 12 with longer laser devices.

FIG. 17 shows the embodiment of the present invention where the lasers 1116, 1118, and 1120 are extended in length. The length of the lasers increases the area of surrounding tissue that can receive the generated laser light.

Figure 18:
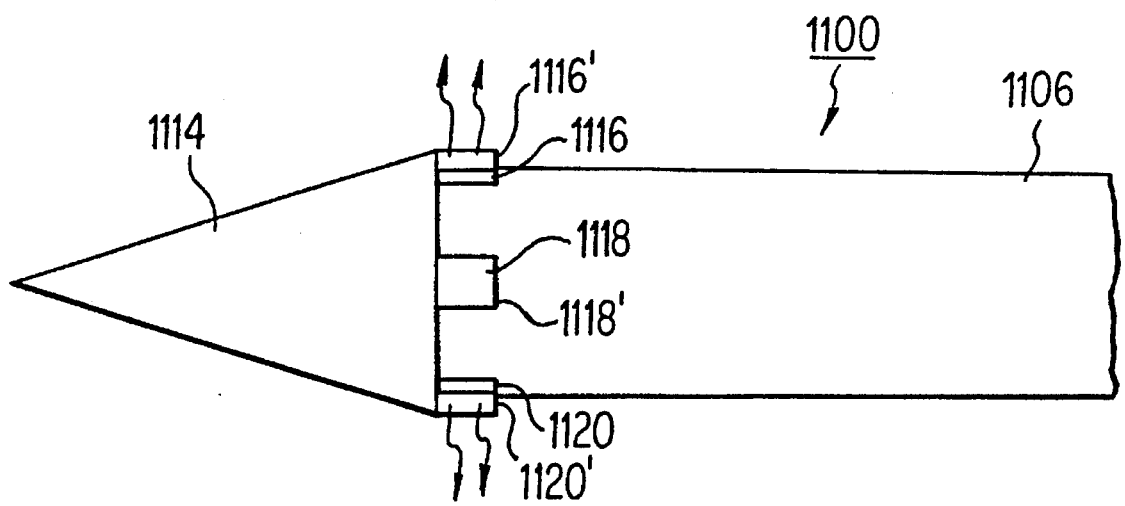
FIG. 18 is a view similar to that of FIG. 11 with thicker or deeper laser devices.

FIG. 18, on the other hand, shows two edge emitting lasers at each location, rather than one longer laser. Laser 1116' is mounted over laser 1116, as are lasers 1118' and 1118, and lasers 1120' and 1120. The laser light from the combined lasers 1116 and 1116' is more intense than a single laser as described above. Either of the lasers shown in FIG. 18 may be substituted by a microwave emitting integrated circuit for the benefit of a combined microwave and laser light ablation effect as may be desired by the operating physician. Microwave frequencies range from megahertz to gigahertz, lower than the frequency of laser light emitted.

Although preferred embodiments of the subject invention have been described in some detail, it is understood by those skilled in the art, that obvious variations can be made herein without departing from the spirit and scope of the invention as defined by the appended claims.

We claim:

1. A medical probe device comprising a catheter having at least one stylet port, at least one flexible stylet disposed within the catheter, means for each stylet outwardly through a stylet port and through intervening tissue to target tissue, each stylet comprising an electrical conductor enclosed within a non-conductive sleeve, and an integrated circuit at the distal ends of the stylets for emitting electromagnetic energy which is delivered as ablative power to the target tissue.

2. The medical probe device of claim 1 wherein each non-conductive sleeve is mounted for longitudinal movement on a respective one of the electrical conductors to expose a selected portion of the electrical conductor surface in the target tissue.

3. The medical probe apparatus of claim 2, wherein the electromagnetic field energy is microwave energy.

4. The medical probe apparatus a set forth in claim 2, wherein the electromagnetic field energy is laser light energy.

5. A medical probe apparatus comprising a catheter having at least one stylet port, a flexible stylet disposed within the catheter, means for advancing the stylet outwardly through the port and through intervening tissue to target tissue, said stylet comprising an electrical conductor, and circuit means at the distal end of the stylet for emitting electromagnetic energy for delivery as ablative power to the target tissue.

6. The medical probe apparatus of claim 5, wherein the electromagnetic energy is microwave energy.

7. The probe apparatus of claim 5 wherein the circuit means comprises at least one semiconductor oscillator means for generating the electromagnetic radiation.

8. The probe apparatus of claim 7 wherein the semiconductor oscillator means comprises an integrated circuit for emitting microwave energy.

9. The probe apparatus of claim 7 wherein the semiconductor oscillator means comprises an integrated circuit for emitting laser light energy.

10. The probe apparatus of claim 5 wherein the circuit means comprises at least two integrated circuit devices located at the distal end of the stylet and spaced apart from each other around the periphery of the stylet.

11. The probe apparatus of claim 10 wherein the integrated circuit devices comprise lasers for radiating the electromagnetic energy in the form of light defining predetermined frequencies.

12. The probe apparatus of claim 11 wherein each of the lasers has first and second electrodes which are coupled to a drive source, with lasers being mounted to the electrical conductor of the stylet, the first electrode and the electrical conductor forming an ohmic contact, and the second electrode forming the closed loop electrode of the laser.

13. The probe apparatus of claim 12 wherein the lasers emit light in a radial direction from the stylet.

14. The probe apparatus of claim 12 where the lasers emit light in a tangential direction from the stylet.

15. The probe apparatus of claim 10 wherein the lasers radiate electromagnetic light energy at separate frequencies.

16. The probe apparatus of claim 10 wherein the integrated circuit devices comprise electrical oscillators for radiating electromagnetic energy having a natural frequency below that of light.

17. The probe apparatus of claim 16 wherein the electrical oscillators radiate electromagnetic energy at separate frequencies below that of light.

18. The probe apparatus of claim 10 wherein at least one of the integrated circuit devices comprises a laser for radiating electromagnetic energy in the form of light of predetermined frequency and at least one other of the integrated circuit devices comprises an electrical oscillator for radiating electromagnetic energy having a natural frequency below that of the light radiated by the laser.

19. The probe apparatus of claim 5 wherein the stylet has a sharp tip at its distal end to facilitate entry into the intervening tissue and the target tissue.

20. The probe apparatus of claim 19 wherein the stylet is a cylindrical tube, the sharp tip has a diameter larger than the tube, and the circuit means comprises a semiconductor oscillator mounted on the cylindrical tube immediately behind the sharp tip.

21. The probe apparatus of claim 20 further including a slot which extends longitudinally of the cylindrical tube for allowing a liquid to flow from the inside of the tube to the outside.

22. The medical probe apparatus of claim 5, wherein the electromagnetic field energy is laser light energy.

23. The medical probe apparatus of claim 5, wherein the electromagnetic field energy comprises laser light energy and microwave energy.

24. The medical probe apparatus of claim 2 wherein the electromagnetic field energy comprises laser light energy and microwave energy.

* * * * *